United States Patent [19]

Suzuki et al.

[11] Patent Number: 4,845,228
[45] Date of Patent: Jul. 4, 1989

[54] PYRIDYL-CYCLOHEXANONE COMPOUNDS

[75] Inventors: Tsuneji Suzuki; Kunio Sannohe; Toshihiko Ito; Masahiko Maruyama, Chiba; Joji Kamiya, Chiba; Makoto Hirayama, Chiba; Takafumi Kitano, Chiba; Akira Awaya, Kanagawa, all of Japan

[73] Assignee: Mitsui Toatsu Chemicals, Inc., Tokyo, Japan

[21] Appl. No.: 148,630

[22] Filed: Jan. 26, 1988

Related U.S. Application Data

[62] Division of Ser. No. 754,286, Jul. 12, 1985.

[30] Foreign Application Priority Data

Jul. 26, 1984 [JP] Japan .................. 59-154108

[51] Int. Cl.$^4$ ........................... C07D 213/50
[52] U.S. Cl. ................... 546/339; 546/340; 546/342
[58] Field of Search ............ 546/339, 340, 342

[56] References Cited

U.S. PATENT DOCUMENTS 4,026,900 5/1977 Gelotte et al. ............ 546/340

FOREIGN PATENT DOCUMENTS 0207500 1/1987 European Pat. Off. ...... 546/112
0291568 12/1986 Japan .......................... 546/340
0291569 12/1986 Japan .......................... 546/340
0010063 1/1987 Japan .......................... 546/340

OTHER PUBLICATIONS

Prostakov et al., Chemical Abstracts, vol. 97, No. 15, Abstract 127,458p, Oct. 11, 1982, p. 709.
Freeman et al., Journal of Organic Chemistry, vol. 33, No. 9, pp. 3648-3650, May 27, 1988.

Primary Examiner—Mary C. Lee
Assistant Examiner—Zima Northington
Attorney, Agent, or Firm—Browdy & Neimark

[57] ABSTRACT

The present invention relates to cyclohexanone derivatives represented by general formula:

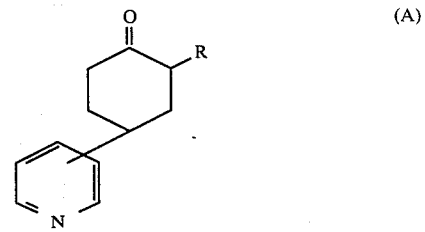

wherein R represents a hydrogen atom or an acetyl group. The cyclohexanone derivatives are important intermediates for producing isoquinoline derivatives which are useful as drugs, especially for heart drugs.

3 Claims, No Drawings

PYRIDYL-CYCLOHEXANONE COMPOUNDS

This is a divisional application of parent copending application Ser. No. 754,286, filed July 12, 1985.

DETAILED DESCRIPTION OF THE INVENTION

1. Field of Industrial Application

The present invention relates to cyclohexanone derivatives and more particularly, to novel pyridine-substituted cyclohexanone derivatives.

The present compounds are novel compounds and are extremely useful as intermediates particularly for synthesis of isoquinoline derivatives useful as medicines.

2. Prior Art

The compounds in accordance with the present invention are intermediates for synthesizing isoquinoline derivatives represented by formula (I)

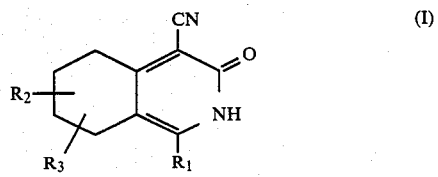

wherein $R_1$ represents a methyl group or a methoxymethyl group and, $R_2$ and $R_3$ represent a hydrogen atom, a lower alkyl group, a lower alkoxy group, a cyclohexyl group, a phenyl group, a substituted phenyl group, a pyridyl group or an oxo group (=O), and are novel compounds that have not been recited in publications.

Problems to be solved by the Invention

At present, digitalis preparations ("IYAKUHIN YO-RAN" (HANDBOOK OF DRUGS), pp. 324–327 (1977), Yakugyo Jihosha) used for treatment require a skill for use due to their narrow safety zone and also encounters a problem of causing side effects such as arrhythmia, etc. Further, nicotinonitrile derivatives, imidazolone derivatives and dihydropyridazinone derivatives, etc., which have been reported recently (Published Unexamined Japanese Patent Application Nos. 70868/82, 155368/84 and 74679/83), involve problems such as a poor cardiotonic activity, a narrow safety zone, an increase in the number of rhythmic movement of heart muscle, high toxicity to animals, etc.

Means for solving the Problems

As a result of extensive investigations to achieve the objects described above, aiming at compounds having a broad safety zone and free from side effects, it has been found that the isoquinoline derivatives shown by formula (I) possess high cardiotonic activity and low toxicity. In order to synthesize the isoquinoline derivatives, various synthesis routes have been investigated and as a result, it has been found out in the present invention that the pyridine-substitute cyclohexanone derivatives shown by formula (A) are useful as intermediates for the synthesis and the present invention has thus come to be accomplished. The cyclohexanone derivatives of the present invention can be prepared, for example, by the following process.

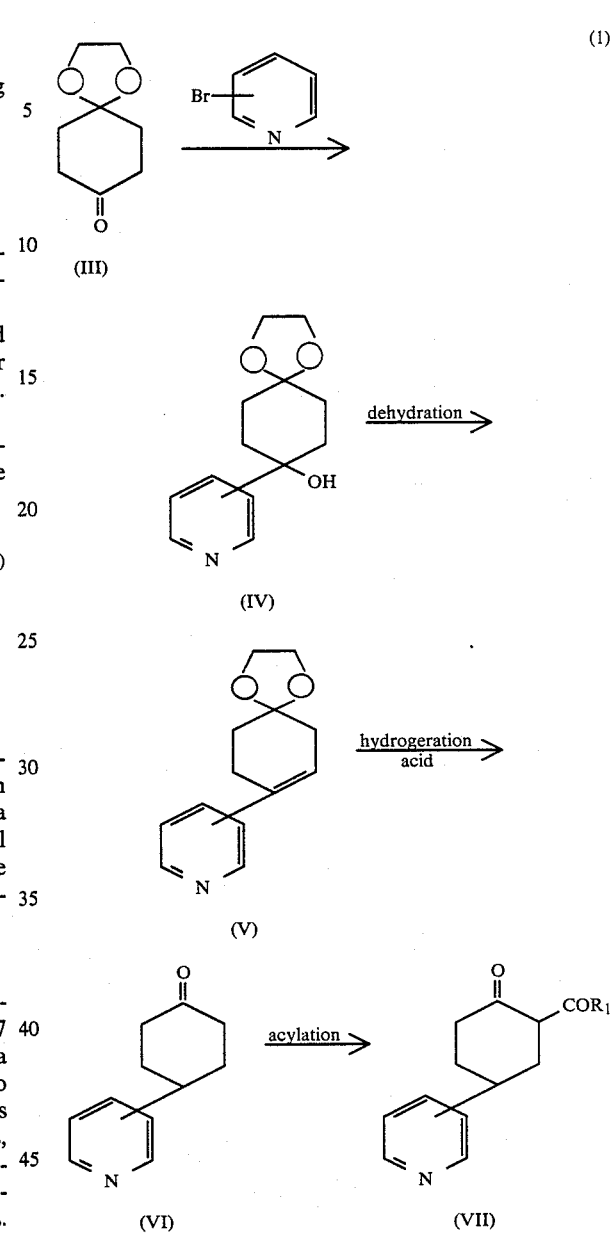

Namely, in reaction scheme (1), 1,4-cyclohexanedione monoethylene ketal (III) is condensed with 2-, 3- or 4-bromopyridine in the presence of n-butyl lithium to produce (IV), then (IV) is reacted, for example, with thionyl chloride in pyridine to prepare (V) and, (V) is hydrogenated in a mineral acid to prepare the desired compound (VI). Subsequently, (VI) can be acylated to prepare another desired compound (VII); in the case of acetylation, it is carried out using an appropriate acetylating agent, i.e., acetylimidazole, acetic anhydride, an acetyl halide or an acetic acid ester, etc. in the presence of a sodium alkoxide, sodium hydride, boron trifluoride-acetic acid, lithium diisopropylamide or zinc chloride, etc. Further, after converting (VI) into the enamine with pyrrolidine, etc., the enamine can also be acetylated with acetic anhydride. Thus, the compounds in accordance with the present invention, for example, (VI) and (VII), can be obtained. These compounds are useful as intermediates for preparing the isoquinoline derivatives shown by formula (I). The isoquinoline derivatives can be prepared, for example, as follows.

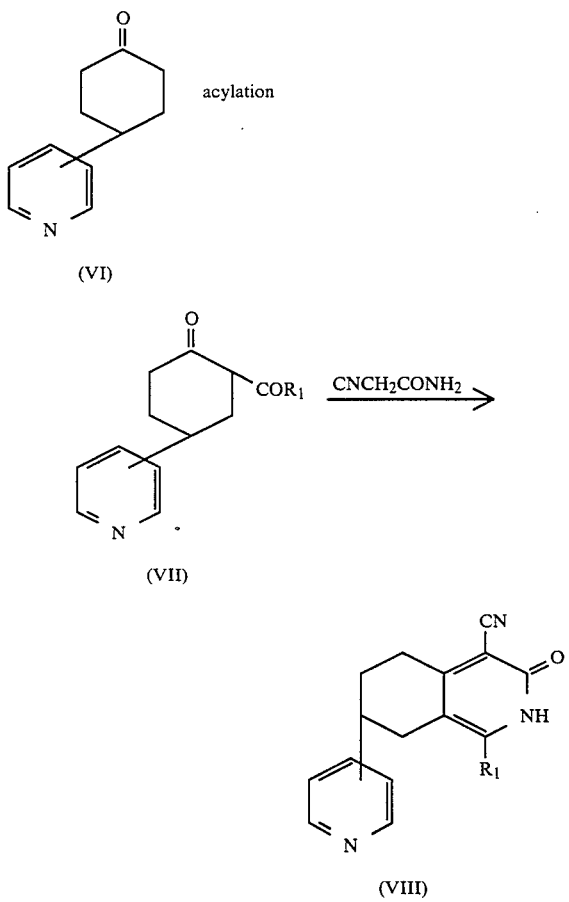

Namely, in reaction equation (2), (VIII) can be prepared by acylating (VI) to give (VII) (they are both included in the compounds (A) of the present invention) and condensing (VII) with cyanoacetamide in an alcohol such as methanol or ethanol, etc. in the presence of, e.g., a secondary amine such as piperidine or diethylamine, etc. or in the presence of a sodium alkoxide. (VIII) is a compound which falls under the final product (I) useful as a medicine.

The novel isoquinoline derivatives shown by formula (I) are useful as drugs, particularly as cardiotonic agents. As their dosage form, oral administration is preferred but parenteral administration may also be used. The derivatives and salts thereof can be formed into various preparations in a manner conventional for making preparations. In the case of oral administration, daily dose is approximately 0.1 to 10 mg per 1 kg of body weight but the dose is not limited thereto. Further these derivatives showed low toxicity; acute toxicity showed $LD_{50}$ of 400 mg/kg or more.

Hereafter processes for preparing the cyclohexanone derivatives in accordance with the present invention will be shown as examples and, processes for preparing the isoquinoline derivatives shown by formula (I) using the cyclohexanone derivatives as raw materials will be shown as reference examples. Further, effectiveness of the derivatives demonstrated by pharmacological experiments will be shown as test examples, respectively.

EXAMPLE 1

4-(4-Pyridyl)cyclohexanone (1) 4-Hydroxy-4-(4-pyridyl)cyclohexanone ethyleneacetal Thirty-five ml of ether was cooled to −78° C., to which 20 ml of a 1.6 mol n-butyl lithium solution in hexane was added. Next, 5 g of 4-bromopyridine was dissolved in 30 ml of ether and the solution was added to the mixture. Then, a solution of 5 g of 1,4-cyclohexanedione monoethyleneacetal in 30 ml of tetrahydrofuran was added to the mixture. After completion of the reaction, the reaction solution was poured into saturated ammonium chloride aqueous solution. The mixture was extracted with chloroform and the extract was purified to give 5 g of 4-hydroxy-4-(4-pyridyl)cyclohexanone ethyleneacetal.

mp 165.5–167.5° C, NMR$\delta_{TMS}^{CDCl_3}$:1.6–2.2(8H, m), 3.9(1H, s), 4.00(4H, s), 7.45(2H, dd), 8.44(2H, dd). (2) 4-(4-Pyridyl)cyclohex-3-enone ethyleneacetal In 40 ml of pyridine was dissolved 5 g of 4-hydroxy-4-(4-pyridyl)cyclohexanone ethyleneacetal and, 8 ml of thionyl chloride was added to the solution at -10° C. Then, after stirring at 0° C., the reaction solution was poured onto ice. After an excess of a sodium hydroxide aqueous solution was added to the mixture, it was extracted with methylene chloride and the extract was purified to give 4 g of 4-(4-pyridyl)cyclohex-3-enone ethyleneacetal.

mp 67–70° C.

NMR$\delta_{TMS}^{CDCl_3}$:1.86(2H, t), 2.4–2.7(4H, m), 4.04(4H, s), 6.24(1H, t), 7.28(2H, d), 8.52(2H, d).

(3) 4-(4-Pyridyl)cyclohexanone

In 70 ml of 0.5N hydrochloric acid was dissolved 4 g of 4-(4-pyridyl)cyclohex-3-enone ethyleneacetal and, 400 mg of 10% palladium-carbon was added to the solution followed by hydrogenation at normal temperature under normal pressure. After completion of the reaction, the catalyst was removed. After the system was rendered alkaline with a sodium hydroxide aqueous solution, it was extracted with methylene chloride to give 2.7 g of 4-(4-pyridyl)cyclohexanone.

NMR$\delta_{TMS}^{CDCl_3}$:1.7–2.3(4H, m), 2.4–2.6(4H, m),2.8-3.2(1H, m), 7.15(2H, d), 8.51(2H, m).

EXAMPLE 2

2-Acetyl-4-(4-pyridyl)cyclohexanone

In 40 ml of tetrahydrofuran was dissolved 3.2 ml of diisopropylamine and, 14.2 ml of 1.6 mol n-butyl lithium solution in hexane was added to the solution at −20° C. Next, a solution of 2 g of 4-(4-pyridyl)cyclohexanone obtained in Example 1 in 40 ml of tetrahydrofuran was added to the mixture at −40° C. The reaction solution was cooled to −78° C., to which a solution of 2.5 g of acetylimidazole in 40 ml of tetrahydrofuran was added. After stirring at room temperature, the reaction solution was poured onto ice. After washing with ether, the aqueous phase was saturated with ammonium chloride and extracted with methylene chloride to give 1.65 g of 2-acetyl-4-(4-pyridyl)cyclohexanone.

NMR$\delta_{TMS}^{CDCl_3}$: 1.7–2.2(3H, m), 2.16(3H, s), 2.3–2.6(3H, m), 2.6–2.9(1H, m), 7.10(2H, dd), 8.55(2H, dd), 15.7(1H,s).

EXAMPLE 3

4-(2-Pyridyl)cyclohexanone (1) 4-Hydroxy-4-(2-pyridyl)cyclohexanone ethyleneacetal 2-Bromopyridine, 5 g, was used instead of 4-bromopyridine in Example 1-(1) and treated as in the case of 4-bromopyridine to give 4.7 g of 4-hydroxy-4-(2-pyridyl)cyclohexanone ethyleneacetal.

NMR$\delta_{TMS}^{CDCl_3}$: 1.5–1.9(4H, m), 1.9–2.4(4H, m), 3.96(4H, s), 7.2(1H, dd), 7.4(1H, d), 7.68(1H, ddd), 8.48(1H, dd).

(2) 4-(2-Pyridyl)cyclohex-3-enone ethyleneacetal

4-Hydroxy-4-(2-pyridyl)cyclohexanone ethyleneacetal, 4.6 g, was used and treated as in Example 1-(2) to give 3.3 g of 4-(2-pyridyl)cyclohex-3-enone ethyleneacetal.

NMR$\delta_{TMS}^{CDCl_3}$: 1.92(2H, t), 2.4–2.56(2H, m), 2.64–2.82(2H, m), 3.96(4H, s), 6.44–6.60(1H, m), 7.12(1H, dd), 7.36(1H, d), 7.58(1H, ddd), 8.52(1H, dd).

(3) 4-(2-Pyridyl)cyclohexanone 4-(2-Pyridyl)cyclohex-3-enone ethyleneacetal, 3.3 g, was used and treated as in Example 1-(3) to give 2.2 g of 4-(2-pyridyl)cyclohexanone.

NMR$\delta_{TMS}^{CDCl_3}$: 1.8–2.6(8H, m), 3.0–3.32(1H, m), 7.0-7.3(2H, m), 7.62(1H, ddd), 8.48(1H, dd)

EXAMPLE 4

2-Acetyl-4-(2-pyridyl)cyclohexanone 4-(2-Pyridyl)cyclhexanone, 1.9 g, was used and treated as in Example 2 to give 2-acetyl-4-(2-pyridyl)cyclohexanone. This compound can be used at the following step in the whole amount in a crude state thereof.

EXAMPLE 5

4-(3-Pyridyl)cyclohexanone (1) 4-Hydroxy-4-(3-pyridyl)cyclohexanone ethyleneacetal 3-Bromopyridine, 5 g, was used in place of 4-bromopyridine in Example 1-(1) and treated as in the case of 4-bromopyridine to give 3.5 g of 4-hydroxy-4-(3-pyridyl)cyclohexanone ethyleneacetal.

NMR$\delta_{TMS}^{CDCl_3}$: 1.56–2.52(8H, m), 3.3(1H,s), 3.94(4H, s), 7.24(1H, dd), 7.84(1H, ddd), 8.36(1H, dd), 8.68(1H, d).

(2) 4-(3-Pyridyl)cyclohex-3-enone ethyleneacetal

4-Hydroxy-4-(3-pyridyl)cyclohexanone ethyleneacetal, 3.5 g, was used and treated as in Example 1-(2) to give 2.6 g of 4-(3-pyridyl)cyclohex-3-enone ethyleneacetal.

NMR$\delta_{TMS}^{CDCl_3}$: 1.82(2H, t), 2.4–2.52(2H, m), 2.52–2.76(2H, m), 3.98(4H, s), 5.96–6.08(1H, m), 7.24(1H, dd), 7.64(1H, ddd) 8.44 (1H, dd), 8.64(1H, d).

(3) 4-(3-Pyridyl)cyclohexanone 4-(3-Pyridyl)cyclohex-3-enone ethyleneacetal, 2.6 g, was used and treated as in Example 1-(3) to give 4-(3-pyridyl)cyclohexanone.

NMR$\delta_{TMS}^{CDCl_3}$: 1.7–2.7(8H, m), 2.92–3.3(1H, m), 7.44(1H, dd), 7.54(1H, ddd), 8.44(1H, dd), 8.5(1H, d).

EXAMPLE 6

2-Acetyl-4-(3-pyridyl)cyclohexanone 4-(3-Pyridyl)cyclohexanone was used and treated as in Example 2 to give 2-acetyl-4-(3-pyridyl)cyclohexanone. This compound can be used at the following step in the whole amount in a crude state thereof.

REFERENCE EXAMPLE 1

4-Cyano-2,3,5,6,7,8-hexahydro-1-methyl-3-oxo-7-(4-pyridyl)isoquinoline

In ethanol were dissolved 1.65 g of 2-acetyl-4-(4-pyridyl)cyclohexanone obtained in Example 1 and 0.64 g of cyanoacetmmide. A small quantity of piperidine was added to the solution and the mixture was heated to reflux for 7 hours. After completion of the reaction, the precipitated crystals were taken out by filtration to give 0.7 g of 4-cyano-2,3,5,6,7,8-hexahydro-1-methyl-3-oxo-7-(4-pyridyl)isoquinoline.

mp 310° C (decomposed).

NMR$\delta_{TMS}^{DMSO-d_6}$: 1.7–2.1(2H, m), 2.22(3H, s), 2.3–2.76(2H, m), 2.8–3.0(3H, m), 7.35(2H, dd), 8.50(2H, dd).

REFERENCE EXAMPLE 2

4-Cyano-2,3,5,6,7,8-hexahydro-1-methyl-3-oxo-7-(2-pyridyl)isoquinoline

Crude 2-acetyl-4-(2-pyridyl)cyclohexanone obtained in Example 4 was used in the whole amount and treated as in Reference Example 1 to give 0.76 g of 4-cyano-2,3,5,6,7,8-hexahydro-1-methyl-3-oxo-7-(2-pyridyl)isoquinoline.

mp >300° C.

NMR$\delta_{TMS}^{DMSO-d_6}$:1.8–2.2(2H, m), 2.24(3H, s), 2.4–2.6(2H, m), 2.8–3.1(3H, m), 7.2–7.5(2H, m), 7.76(1H, m), 8.54(1H, m), 12.3(1H, s).

REFERENCE EXAMPLE 3

4-Cyano-2,3,5,6,7,8-hexahydro-1-methyl-3-oxo-7-(3-pyridyl)isoquinoline

Crude 2-acetyl-4-(3-pyridyl)cyclohexanone obtained in Example 6 was used in the whole amount and treated as in Reference Example 1 to give 0.57 g of 4-cyano-2,3,5,6,7,8-hexahydro-1-methyl-3-oxo-7-(3-pyridyl)isoquinoline.

mp >300° C.

NMR$\delta_{TMS}^{DMSO-d_6}$: 1.7–2.1(2H, m), 2.22(3H, s), 2.3–2.76(2H, m), 2.76–3.1(3H, m), 7.36(1H, dd), 7.72(1H, ddd), 8.42(1H, dd), 8.52(1H, d).

REFERENCE EXAMPLE 4

4-Cyano-2,3,5,6,7,8-hexahydro-7-methoxy-1-methyl-3-oxoisoquinoline (1) 2-Acetyl-4-methoxycyclohexanone To 2.5 g of ethyl acetate was added 1.12 g of 60% sodium hydride and, a solution of 1.78 g of 4-methoxycyclohexanone in benzene was added to the mixture. After reacting at 40° C. for 3 hours, methanol was added to decompose an excess of sodium hydride, which was poured into water. The mixture was neutralized with hydrochloric acid ahd extracted with ether to give 1.02 g of 2-acetyl-4-methoxycyclohexanone.

NMR$\delta_{TMS}^{CDCl_4}$: 2.06(3H, s), 1.7–2.5(8H, s), 3.28(3H, s), 3.4(1H, m), 15.9(1H, s).

(2)
4-Cyano-2,3,5,6,7,8-hexahydro-7-methoxy-1-methyl-3-oxoiso-quinoline

With 5 ml of ethanol were mixed 1.02 g of 2-acetyl-4methoxycyclohexanone and 0.462 g of cyanoacetamide and, a small quantity of piperidine was added to the mixture followed by heating to reflux for 2 hours. The precipitated crystals were taken out by filtration and recrystallized from methanol to give 0.42 g of 4-cyano-2,3,5,6,7,8-hexahydro-7-methoxy-1-methyl-3-oxoisoquinoline.

mp 257°–259° C.

NMR$\delta_{TMS}^{CF_3COOH}$: 2.25(2H, m), 2.57(3H, s), 2.97(2H, m), 3.20(2H, m), 3.66(3H, s), 4.16(1H, m).

REFERENCE EXAMPLE 5

4-Cyano-1,7-dimethyl-2,3,5,6,7,8-hexahydro-3-oxoisoquinoline (1) 2-Acetyl-4-methylcyclohexanone·

40% Boron trifluoride-acetic acid complex, 24 g, was chilled with ice and a mixture of 5.6 g of 4-methylcyclohexanone and acetic anhydride was dropwise added to the complex. After stirring at room temperature for 4 hours, approximately 50 ml of saturated sodium acetate aqueous solution was added to the mixture followed by heating to reflux for 1 hour. After cooling, the reaction mixture was extracted with ether and the extract was washed with a sodium bicarbonate aqueous solution and then water. Thereafter, the system was dried and ether was removed by distillation. The obtained 2-acetyl-4-methylcyclohexanone was used in the whole amount at the following step in a crude state thereof.

(2)
4-Cyano-1,7-dimethyl-2,3,5,6,7,8-hexahydro-3-oxoisoquinoline

To the whole amount of crude 2-acetyl-4-methylcyclohexanone obtained in (1) were added 35 ml of ethanol, 3.36 g of cyanoacetamide and a small quantity of piperidine followed by heating to reflux for 4 hours. The precipitated crystals were taken out by filtration and recrystallized from a solvent mixture of methanol and water to give 4.22 g of 4-cyano-1,7-dimethyl2,3,5,6,7,8-hexahydro-3-oxoisoquinoline.

mp >290° C.

NMR$\delta_{TMS}^{CF_3COOH}$: 1.23(3H, d), 2.60(3H, s), 1.8-3.3(7H, m).

REFERENCE EXAMPLE 6

4-Cyano-2,3,5,6,7,8-hexahydro-1-methyl-3-oxo-7-phenylisoquinoline (1) 2-Acetyl-4-phenylcyclohexanone 40% Boron trifluoride-acetic acid complex, 5.5 g, was ice-cooled and a mixture of 2 g of 4-phenylcyclohexanone and 2.35 g of acetic anhydride was dropwise added to the complex. After stirring for 30 minutes under ice cooling and at room temperature for 4 hours, 10 ml of saturated ammonium acetate aqueous solution was added to the mixture followed by stirring at 80° C for 1.5 hours. The reaction mixture was extracted with ether and the extract was purified to obtain 1.77 g of 2-acetyl-4-phenylcyclohexanone.

mp 53-54° C.

NMR$\delta_{TMS}^{DMSO-d6}$: 1.90(3H, m), 2.10(3H, s), 2.50(6H, m), 7.26(5H, s), 10.58(1H, s).

(2)
4-Cyano-2,3,5,6,7,8-hexahydro-1-methyl-3-oxo-7-phenyliso-quinoline

2-Acetyl-4-phenylcyclohexanone, 1.68 g, 0.73 g of cyanoacetamide and a small quantity of piperidine were mixed with 10 ml of ethanol followed by heating to reflux for 2 hours. After cooling, the precipitated crystals were taken out by filtration and purified to give 1.5 g of 4-cyano-2,3,5,6,7,8-hexahydro-1-methyl-3-oxo-7-phenylisoquinoline.

mp >290° C.

NMR$\delta_{TMS}^{DMSO-d6}$: 1.90(3H, m), 2.20(3H, s), 2.80(4H, m), 7.28(5H, s), 12.14(1H, s).

REFERENCE EXAMPLE 7

4-Cyano-2,3,5,6,7,8-hexahydro-1-methoxymethyl-7-methyl-3oxoisoquinoline (1) 2-Methoxyacetyl-4-methylcyclohexanone In 50 ml of benzene was suspended 2.5 g of 60% sodium hydride. While cooling the suspension, a mixture of 5.6 g of 4-methylcyclohexanone and 5.4 g of ethyl methoxyacetate was dropwise added thereto. After stirring at room temperature for 2 hours, 20 ml of water was added thereto and the pH was rendered 3 with concentrated hyrochloric acid. The benzene phase was separated and the aqueous phase was extracted with ether. The benzene solution and the ether solution were combined with each other followed by washing with a sodium chloride aqueous solution. After drying, the mixture was concentrated to give 7.4 g of crude 2-methoxyacetyl-4-methylcyclohexanone. The crude product was used at the following step. (2) 4-Cyano-2,3,5,6,7,8-hexahydro-1-methoxymethyl-7-methyl-3-oxoisoquinoline Crude 2-methoxyacetyl-4-methylcyclohexanone, 3.7 g, 1.68 g of cyanoacetamide and 1 ml of piperidine were mixed with 50 ml of ethanol followed by heating to reflux for 4 hours. The precipitated crystals were taken out by filtration and purified to give 1.5 g of 4-cyano-2,3,5,6,7,8-hexahydro-1-methoxymethyl7-methyl-3-oxoisoquinoline.

mp 205-208° C.

NMR$\delta_{TMS}^{DMSO-d6}$: 1.01(3H, d),1.2-2.0(4H, m), 2.5-2.6(1H, m), 2.7-2.9(2H, m), 3.28(3H, s), 4.32(2H, s), 11.86(1H, s).

Compounds synthesized in a manner similar to Reference Examples 1 through 7 are shown in Table 1.

TABLE 1

| No. | R$_1$ | R$_2$*[1] | R$_3$*[1] | Melting Point (°C.) | NMR($\delta$)*[2] |
|---|---|---|---|---|---|
| 8 | CH$_3$ | 5-CH$_3$ | H | 267 (decpd.) | 1.23(3H, d), 1.5-2.4(7H, m), 2.18(3H, s) |
| 9 | CH$_3$ | 6-CH$_3$ | H | >290 | 1.22(3H, d), 1.3-1.7(1H, m), 1.7-2.3(2H, m), 2.57(3H, s), 2.4-2.9(3H, m) |
| 10 | CH$_3$ | 8-CH$_3$ | H | >300 | 1.07(3H, d), 1.6-1.9(4H, m), 2.28(3H, s) 2.6-3.0(3H, m), 12.16(1H, s) |
| 11 | CH$_3$ | 7-C$_2$H$_5$ | H | 288 (decpd.) | 0.96(3H, t), 1.2-1.6(4H, m), 1.7-2.1(2H, m), 2.24(3H, s), 2.6-2.9(3H, m), 12.2(1H, s) |

TABLE 1-continued

| No. | R₁ | R₂*¹ | R₃*¹ | Melting Point (°C.) | NMR(δ)*² |
|---|---|---|---|---|---|
| 12 | CH₃ | 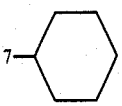 7- | H | 250–252 | 1.0–2.80(18H, s), 2.10(3H, s), 12.0(1H, s) |
| 13 | CH₃ | 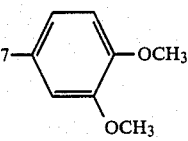 7-〈〉-OCH₃, OCH₃ | H | 293 (decpd.) | 2.39(3H, s), 2.0–3.2(7H, m), 3.84(3H, s), 3.86(3H, s), 6.7–6.9(3H, m), 14.0(1H, s) |
| 14 | CH₃ | 7 = 0 | H | 260 (decpd.) | 2.23(3H, s), 2.48(2H, dd), 3.08(2H, dd), 3.30(2H, s), 12.70(1H, s) |
| 15 | CH₃ | 8 = 0 | H | 218 (decpd.) | 2.0–2.2(2H, m), 2.62(2H, dd), 2.82(3H, s), 3.08(2H, dd), 13.55(1H, s) |
| 16 | CH₃ | 7-OCH₃ | 7-OCH₃ | 280 (decpd.) | 1.92(2H, dd), 2.24(3H, s), 2.58(2H, s), 2.72(2H, dd), 3.16(6H, s), 12.65(1H, s) |
| 17 | CH₃ | 7-OCH₃ | 8 = 0 | 245 (decpd.) | 1.9–2.3(2H, m), 2.62(3H, s), 3.50(2H, dd), 3.28(3H, s), 3.86(1H, dd), 12.40(1H, s) |

*¹:Numerals indicate the position substituted.
*²:Solvent used for measurment:
DMSO—d6: Nos. 8, 10, 11, 12, 14, 16, 17
CDCl₃: Nos. 13, 15
CF₃COOH: No. 9

TEST EXAMPLE 1

Female and male adult mongrel adult dogs weighing 8 to 12 kg intravenously anesthesized with 30 mg/kg of sodium pentobarbital were used. A catheter tip pressure sensor was inserted into the left cardiac ventricle from the right carotid artery to measure the left intraventricular pressure and further a primary differentiation of the left intraventricular pressure was calculated using a differential meter to determine the maximum change rate of the left intraventricular pressure (LV dp/dt max). A polyethylene cannula connected to a pressure transducer was inserted into the right femoral artery to measure the whole blood pressure and the number of heart beats with a pulse meter from its pulse wave, respectively. A drug was administered from the right femoral vein and continuous administration was performed from the left femoral vein. Each parameter was simultaneously recorded on a thermal recorder.

By intravenous administration of propranolol at a dose of 4 mg/kg and continuous intravenous administration at a dose of 0.1 mg/kg/min., a stable heart failure state was created. Namely, it is the state where blood pressure, the number of heart beats and the left intraventricular pressure are somewhat reduced and LV dp/dt is markedly reduced. The dose of a drug which reverted the reduction of this LV dp/dt max to the value prior to administration of propranolol was determined, which was made an effective dose (ED100) The change of blood pressure and the number of heart beats in ED100 was expressed by a rate of change to the values when propranolol was administered.

TABLE 2

| No.*¹ | ED₁₀₀ (mg/kg, i.v.) | Blood Pressure (%) | Number of Heart Beat (%) |
|---|---|---|---|
| 1 | 0.1 | 8.7 | 27.6 |
| 2 | 0.1 | −5.1 | 18.7 |
| 3 | 0.1 | 11.3 | 26.1 |
| 4 | 1.0 | −16.7 | 22.1 |
| 5 | 0.3 | −24.6 | 25.5 |
| 6 | 0.1 | 4.0 | 11.0 |
| 7 | 3.0 | −11.8 | 18.8 |
| 8 | 1.0 | −6.7 | 20.0 |
| 9 | 1.0 | −11.9 | 24.8 |
| 10 | 3.0 | −28.3 | 31.1 |
| 11 | 0.3 | −10.8 | 24.5 |
| 12 | 0.1 | −16.8 | 13.6 |
| 13 | 1.0 | −21.6 | 34.4 |
| 14 | 3.0 | −18.5 | 26.7 |
| 15 | 3.0 | −17.1 | 21.6 |
| 16 | 0.3 | −10.0 | 31.4 |
| 17 | 3.0 | −20.7 | 24.2 |

*¹: Nos. 1 through 7 indicate numbers of Reference Examples and Nos. 8 through 17 indicate numbers of Table 1.

Effects of the Invention

The present invention relates to novel cyclohexanone derivatives shown by formula (A) and utilizing them, novel isoquinoline derivatives can be prepared.

It has also been found that the thus prepared novel isoquinoline derivatives are useful as cardiotonic agents and low toxic compounds having a broad safety zone. The usefulness as cardiotonic agents can be noted by the effectiveness thereof in standard pharmacological test methods, and it is proven, for example, by significant recovery of heart functions under anesthesia, which has been reduced by intravenous administration of propranolol.

What is claimed is:

1. A cyclohexanone compound represented by formula:

2. A cyclohexanone compound of the formula:

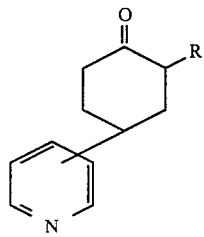
(A)

wherein R represents a hydrogen atom or an acetyl group.

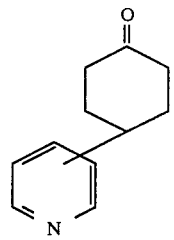
(VI)

or

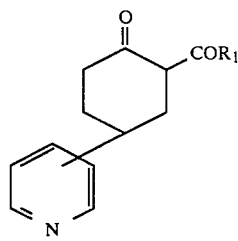
(VII)

wherein $R_1$ is a methyl or methoxymethyl group.

3. A cyclohexanone compound selected from the group consisting of 4-(4-pyridyl) cyclohexanone; 2-acetyl-4-(4-pyridyl) cyclohexanone; 4-(2-pyridyl) cyclohexanone; 2-acetyl-4-(2-pyridyl) cyclohexanone; 4-(3-pyridyl) cyclohexanone; and 2-acetyl-4-(3-pyridyl) cyclohexanone.

* * * * *